(12) United States Patent
Johnson et al.

(10) Patent No.: US 6,512,155 B1
(45) Date of Patent: Jan. 28, 2003

(54) PROCESS FOR THE ACTIVATION OF AN ALKYLAROMATIC ISOMERIZATION CATALYST BY WATER

(75) Inventors: James A. Johnson, Clarendon Hills, IL (US); Benjamin D. Riley, Chicago, IL (US); Sanjay B. Sharma, Burr Ridge, IL (US); Patrick J. Silady, Niles, IL (US); Gail L. Gray, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/556,811

(22) Filed: Apr. 25, 2000

(51) Int. Cl.[7] .................................................. C07C 5/22
(52) U.S. Cl. ....................... 585/481; 585/482; 585/477; 585/480
(58) Field of Search ................................ 585/477, 480, 585/481, 486; 502/326, 327, 333, 334, 337

(56) References Cited

U.S. PATENT DOCUMENTS

| | | | |
|---|---|---|---|
| 3,381,048 A | 4/1968 | Lovell | 260/668 |
| 3,856,872 A | 12/1974 | Morrison | 260/668 |
| 3,898,297 A | 8/1975 | Sampson et al. | 260/668 |
| 4,218,573 A | 8/1980 | Tabak et al. | 585/481 |
| 4,269,813 A * | 5/1981 | Klotz | 423/277 |
| 4,300,013 A | 11/1981 | Whittam | 585/481 |
| 4,431,857 A * | 2/1984 | Feinstein | 585/477 |
| RE31,782 E | 12/1984 | Olson et al. | 585/481 |
| 4,584,423 A | 4/1986 | Nacamuli et al. | 585/481 |
| 4,723,050 A | 2/1988 | Bulter et al. | 585/480 |
| 4,740,650 A | 4/1988 | Pellet et al. | 585/480 |
| 4,899,012 A | 2/1990 | Sachtler et al. | 585/482 |
| 5,276,236 A | 1/1994 | Patton et al. | 585/482 |
| 5,321,184 A * | 6/1994 | Iow et al. | 585/481 |
| 5,773,679 A | 6/1998 | Beck et al. | 585/475 |
| 5,898,090 A | 4/1999 | Hammerman et al. | 885/477 |

FOREIGN PATENT DOCUMENTS

| | | | |
|---|---|---|---|
| DE | 219 183 A1 | 11/1983 | C07C/15/08 |
| GB | 1255459 | 12/1971 | 260/116 |

OTHER PUBLICATIONS

Meier and Olson, 1992, "Atlas of Zeolite Structure Types", pp. 138, 139, and 193.*

* cited by examiner

*Primary Examiner*—Thuan Dang
(74) *Attorney, Agent, or Firm*—John G. Tolomei; Frank S. McLinaro; Thomas K. McBride, Jr.

(57) ABSTRACT

An improved process is disclosed for ethylbenzene and xylene isomerization in a non-equilibrium mixture of xylenes and ethylbenzene. By addition of trace quantities of water to the reaction zone, equivalent isomerization is effected at lower temperatures wherein benefits could be realized in reduced losses and improved catalyst life.

20 Claims, 2 Drawing Sheets

PROCESS FOR THE ACTIVATION OF AN ALKYLAROMATIC ISOMERIZATION CATALYST BY WATER

FIELD OF THE INVENTION

This invention relates to a process for isomerization of alkylaromatics. The process involves contacting the alkylaromatics with a catalyst at isomerization conditions with water.

BACKGROUND OF THE INVENTION

The xylenes, i.e., para-xylene, metaxylene and orthoxylene, are important intermediates which find wide and varied application in chemical synthesis. Para-xylene upon oxidation yields terephthalic acid which is used in the manufacture of synthetic textile fibers and resins. Metaxylene is used in the manufacture of plasticizers, azo dyes, wood preservers, etc. Orthoxylene is feedstock for phthalic anhydride production.

Xylene isomers from catalytic reforming or other sources generally do not match demand proportions as chemical intermediates, and further contain ethylbenzene which is difficult to separate or convert. Para-xylene in particular is a major chemical intermediate with rapidly growing demands, but amounts to only 20–25% of a typical $C_8$ aromatics stream. Adjustment of isomer ratio to demand can be effected by combining xylene-recovery, such as adsorption for para-xylene recovery, with isomerization to yield an additional quantity of the desired isomer. Isomerization converts a non-equilibrium mixture of the xylene isomers which is lean in desired components to a mixture approaching equilibrium concentrations.

An increasingly close approach to equilibrium of $C_8$ aromatic isomers in an isomerization process is associated with higher losses of $C_8$ aromatics to other hydrocarbons. A close approach to equilibrium minimizes the amount of recycle to para-xylene recovery, and thus reduces the investment and operating costs of the complex. A lower loss of $C_8$ arornatics reduces feedstock requiremnents, and increasesi the proportion of higher-value products. The performance of an isomerization process is determined principally by the interrelationship of conversion, $C_8$ aromatic losses and catalyst stability. The operating temperature required to achieve a given conversion is an indicator of such performance, since higher temperatures generally result in higher losses to byproducts and more rapid catalyst deactivation.

Catalysts for the upgrading of $C_8$ aromatics to improve isomer distribution ordinarily are characterized by the manner of processing ethylbenzene associated with the xylene isomers. Ethylbenzene is not easily isomerized to xylenes, but it normally must be reacted because separation from the xylenes by superfractionation or adsorption is very expensive. Modern approaches to $C_8$ aromatics isomerization include reaction of the ethylbenzene in the presence of a solid acid catalyst with a hydrogenation-dehydrogenation function to effect hydrogenation to a naphthene intermediate followed by dehydrogenation to form a xylene mixture. Another approach is to convert ethylbenzene via dealkylation to form principally benzene while isomerizing xylenes to a near-equilibrium mixture. The former approach enhances xylene yield by forming xylenes from ethylbenzene, but the latter approach commonly effects higher ethylbenzene conversion and thus lowers the quantity of recycle to the para-xylene recovery unit with a concomitant reduction in processing cost. The latter approach also yields a high-quality benzene product.

U.S. Pat. No. 4,899,012 (Sachtler et al.), teaches the process of ethylbenzene dealkylation and xylene isomerization using the pentasil group (MFI, MEL, MTW, MTT and FER) of zeolitic aluminosilicates. U.S. Pat. No. 4,740,650 (Pellet et al.) teaches isomerization using at least one non-zeolitic molecular sieve which preferably is a silicoalurninophosphate. U.S. Pat. No. 5,276,236 (Patton et al.) discloses a MgAPSO non-zeolitic molecular sieve and its use in the process of alkylaromatic isomerization. U.S. Pat. No. 5,898,090 (Hammerman et al.) teaches isomerization of a mixture of xylenes and ethylbenzene using an SM-3 silicoaluminophosphate molecular sieve.

In the isomerization art relating to combination schemes, in which the isomerization process is disclosed in the context of product recovery technology, there is a strong implication that the isomeriationfeed will be dry. For example. U.S. Pat. Nos. 3,856,872 (Morrison), 4,218,573 (Tabak et al.) and Re 31,782 (Olson et al.) disclose various flow schemes including a crystallizer providing feedstock to the isomerization process. It is known in the art that a crystallizer recovering para-xylene must be a dry operation, and the raffinate from the crystallizer to the isomerization process thus will be dry. U.S. Pat. No. 4,584,423 (Nacamuli et al.) discloses prefractionation and crystallization prior to isomerization, and both steps would remove water from the isomerization feed.

U.S. Pat. No. 4,300,013 (Whittam), on the other hand, discloses the addition of large quantities of water (0.05–1.0 wt. %) in an alkylbenzene isomerization process based on zeolite FU-1. U.S. Pat. No. 4,723,050 (Butler et al.) also discloses the supply of large quantities of water (0.1–10 wt. %) to an isomerization process based on the idea that steam is believed to reduce catalyst coking due to sulfur.

U.K. Patent Specification 1,255,459 (Hart et al.) discloses steam addition in an amount ranging from 100 to 1500 ppm for an xylene isomerization process. Hart et al. discloses ethylbenzene isomerization to xylenes through naphthenes using a catalyst based on an acidic refractory oxide containing a mixture of silica and alumina. Also disclosed is the use of zeolitic aluminosilicates such as faujasite (FAU).

German Patent DD-219,183 (Doms et al.) discloses a mordenite (MOR) based catalyst contacted with NH3, where the selectivity of ethylbenzene isomerization is improved by the addition of 500 to 800 ppm water in the initial reaction period up to a running time of 300 hours followed by reduction of the water content to the range of 10 to 50 ppm.

Other disclosures of the art include U.S. Pat. No. 3,381,048 (Lovell et al.) and U.S. Pat. No. 3,898,297 (Sampson et al.) both of which are based on amorphous catalyst systems. Lovell et al. disclose for a xylene isomerization process based on a platinum-alumina-halogen catalyst system that process conditions be controlled so that water content is dry on the order of 20 to 200 wt-ppm during reaction and wet on the order of 0.3 to 2.0 wt % during regeneration. Sampson et al. disclose an alkyl benzene isomerization process based on fluorided variations of amorphous aluminas or silica/aluminas optionally containing alkali or alkaline earth metals in the presence of steam in the range of 0.005 to 1.0 wt %.

U.S. Pat. No. 4,431,857 (Feinstein) discloses the use of crystalline borosilicate (AMS-1B) impregnated with molybdenums and the use of water addition to favor $A_{10}$ formation via a disproportionation mechanism.

U.S. Pat. No. 5,773,679 (Beck et al.) discloses the co-feeding of water during the initial operation of selectivated ZSM type zeolites for hydrocarbon conversion, and the use of silicon treated ZSM-5 for toluene disproportionation in particular. The effect of this zeolite treatment is to increase para-selectivity of the catalyst by decreasing the yield of xylenes, with the total xylenes decreasing a greater amount than the para-isomer such that the relative ratio of para-xylene increases, and with the resultant balance showing increased yield of benzene. No effect on ethyl-benzene conversion is shown.

Nothing in the prior art suggests the use of trace quantities of water injection during alkylaromatic isomerization reaction conditions with non-zeolitic molecular sieve containing catalysts in order to effect improved or reactivated catalyst performance while maintaining the presence of hydrocarbon material in the system. Further, the need to improve the use selected pentasil zeolitic aluminosilicate containing catalysts that have not been silicon selectivated and where the water injection may be provided continuously or intermittently to promote favorable ethylbenzene conversion also is addressed by the present invention.

SUMMARY OF THE INVENTION

In summary, it is an object of the present invention to provide an improved process for the isomerization of xylenes and conversion of ethylbenzene.

This invention is based on the discovery that injection of trace amounts of water or a water producing compound into the reactor zone of a $C_8$ aromatics isomerization process results in a surprising improvement in ethylbenzene conversion and para-xylene yield at given reactor temperatures, along with improved catalyst stability.

A broad embodiment of the present invention is a process for the upgrading of a nonequilibrium $C_8$ aromatics feed mixture wherein water or a water forming compound is supplied continuously or intermittently to a reaction zone containing a catalyst comprising either a non-zeolitic molecular sieve or a pentasil zeolitic aluminosilicate in order to increase xylenes isomerization and ethylbenzene conversion at a given temperature.

In a specific embodiment, the catalyst further comprises at least one platinum-group metal component, and an inorganic-oxide binder. The equivalent water provided to the reaction zone corresponds to about 75 to about 750 mass ppm, or preferably corresponds to about 100 to about 500 mass ppm.

These as well as other objects and embodiments will become apparent upon a reading of the following detailed description of the invention.

BRIEF DESCRIPTION OF THE DRAWINGS

FIG. I compares the product ratio of para-xylene in total xylenes relative to reaction temperature when converting ethylbenzene in conjunction with xylene isomerization with and without the provision of a trace quantity of water to the reaction zone.

FIG. II compares ethylbenzene dealkylation as a function of temperature to show the effect of trace water addition.

DETAILED DESCRIPTION OF THE INVENTION

Figure 1:
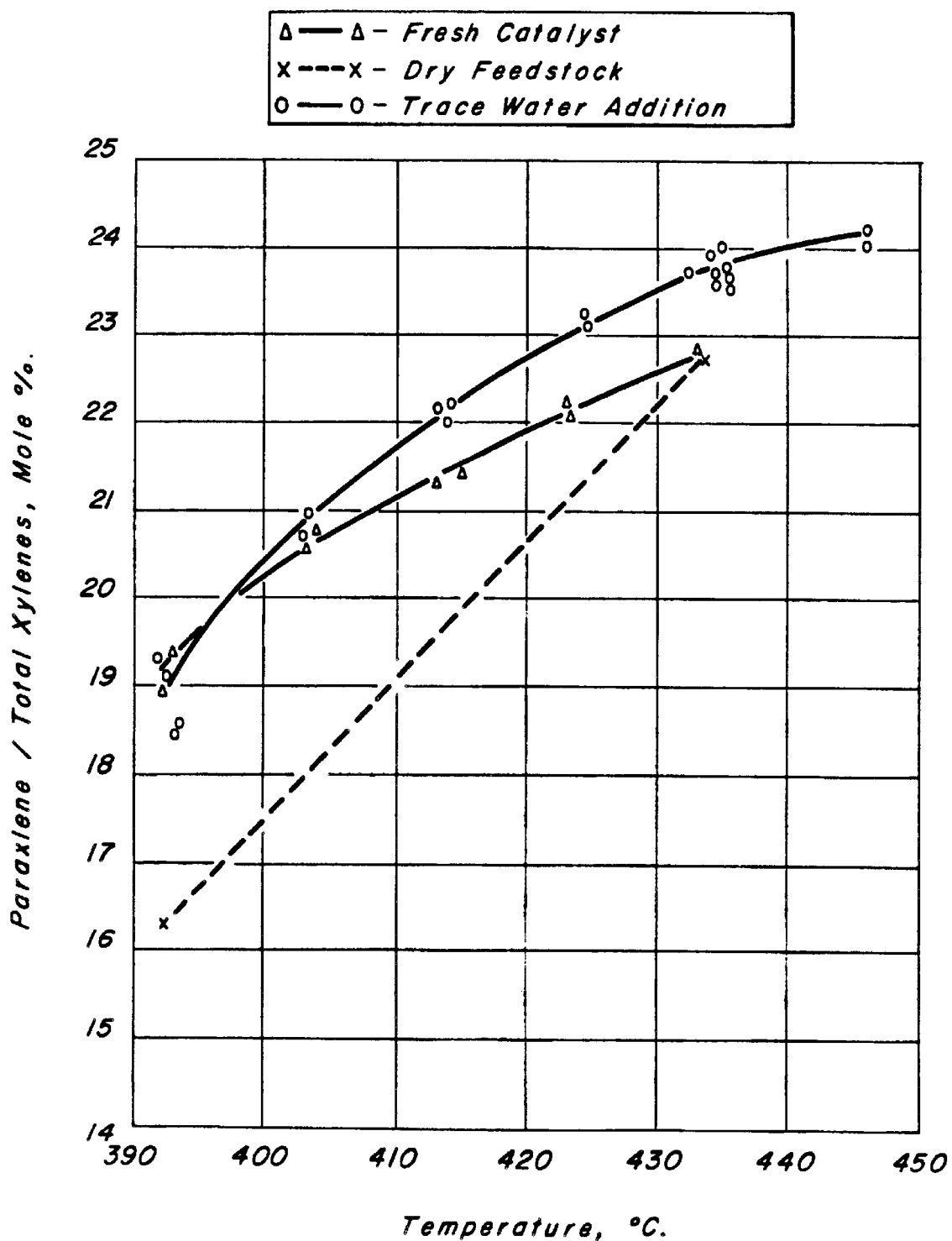
Figure 2:
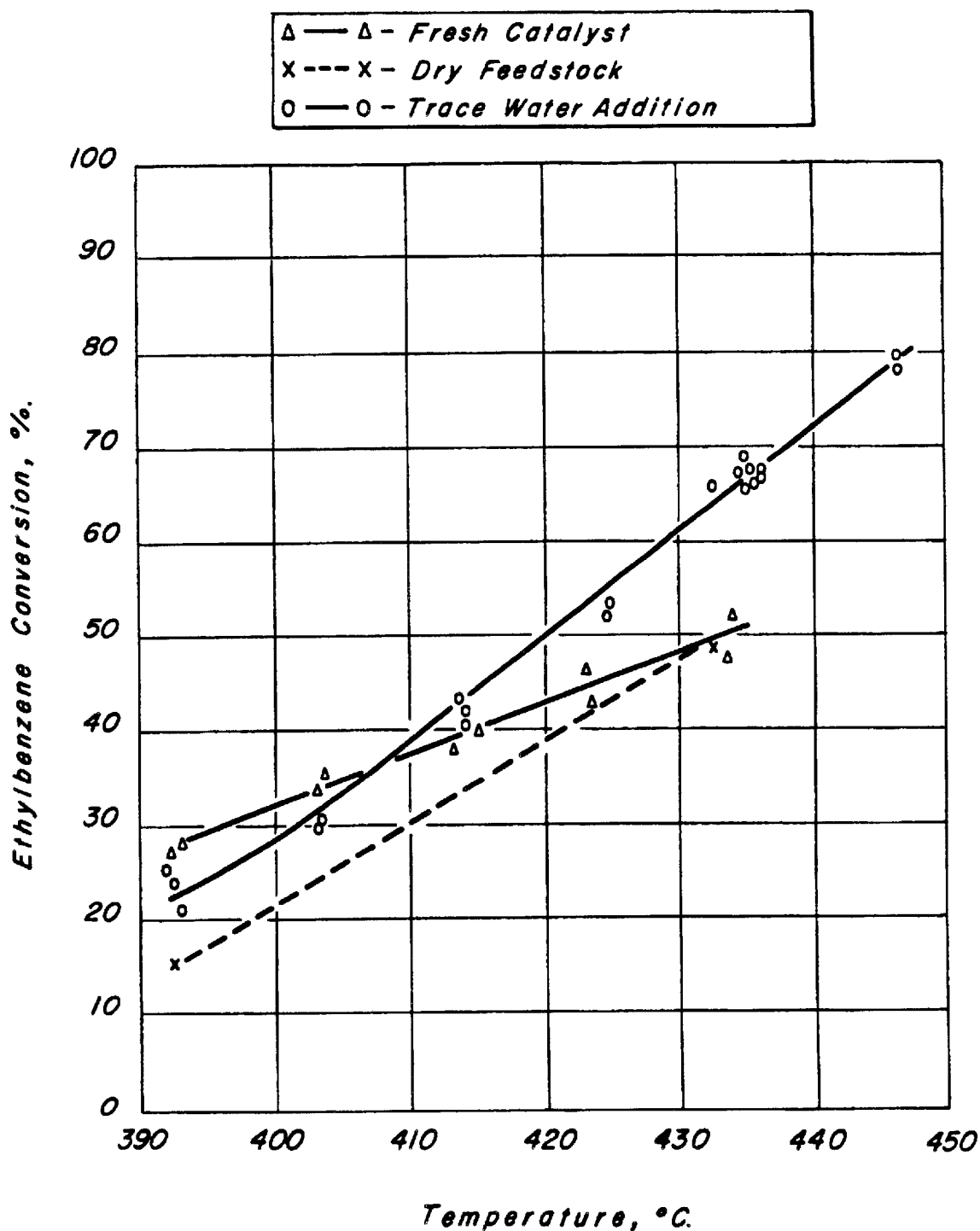

A feedstock to the present process comprises alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof. Preferred isomerizable alkylaromatic hydrocarbons include the xylene isomers in admixture with ethylbenzene as a nonequilibrium mixture.

The present process effects conversion of $C_2H_5$, $C_3H_7$, and higher R groups on aromatic rings via dealkylation in conjunction with isomerization of methyl side chains on aromatic rings to approach a near-equilibrium isomer distribution in the aromatics product from the process.

The alkylaromatic hydrocarbon feedstock may be utilized as found in selected fractions from various refinery petroleum streams, e.g., as recovered from catalytic reformate by fractionation or solvent extraction, produced as a byproduct of pyrolysis of petroleum distillates to obtain principally light olefins, or recovered from cracking of heavy petroleum fractions principally to gasoline-range products. An especially preferred feedstock is the raffinate after recovery of one or more valuable $C_8$ aromatic isomers, e.g., the recovery of para-xylene by adsorption or crystallization and/or the recovery of orthoxylene by fractionation. Usually the feedstock will be substantially sulfur-free, generally containing less than 1 mass ppm sulfur due to prior catalytic processing. The isomerizable aromatic hydrocarbons which are converted in the process of this invention need not be concentrated. By increasing the yield of valuable petrochemical intermediates from streams which otherwise could command only fuel value, the profitability of such petrochemical operations can be enhanced.

According to the process of the present invention, an alkylaromatic hydrocarbon feedstock, preferably in admixture with hydrogen, is contacted with a catalyst of the type hereinafter described in a reaction zone. Contacting may be effected using the catalyst in a fixed-bed system, a moving-bed system, a fluidized-bed system, or in a batch-type operation. In view of the danger of attrition loss of the valuable catalyst and of operational advantages, it is preferred to use a fixed-bed system. In this system, a hydrogen-rich gas and the feedstock are preheated by suitable heating means to the desired reaction temperature and the combined reactants then pass into a reaction zone containing a fixed bed of the catalyst. The reaction zone may be one or more separate reactors with suitable means therebetween to ensure that the desired isomerization temperature is maintained at the entrance to each reactor. It is to be noted that the reactants may be contacted with the catalyst bed in either upward, downward, or radial-flow fashion, and that the reactants may be in the liquid phase, a mixed liquid-vapor phase, or a vapor phase when contacted with the catalyst.

Operating conditions in the reaction zone include a temperature in the range from about 0° to about 600° C. and a pressure from a atmospheric to about 5MPa Preferably a temperature range of about 300° to 500° C. and a pressure range of about 1 to 50 atmospheres is employed. The liquid hourly hydrocarbon space velocity of the feedstock relative to the volume of catalyst is from about 0.1 to about 30 hr–1, and most preferably at 0.5 to 15 $hr^{-1}$. The hydrocarbon is passed into the reaction zone preferably in admixture with a gaseous hydrogen-containing stream at a hydrogen-to-hydrocarbon mole ratio of from about 0.5:1 to 15:1 or more, and preferably a ratio of from about 0.5 to 10. Other inert diluents such as nitrogen, argon, methane, ethane, and the like may be it present.

It is an essential aspect of the invention that trace quantities of water are supplied to the reaction zone of the present process. Trace quantities generally will amount to no more than the water of saturation of the alkylaromatic feedstock, or typically up to about 750 mass ppm (parts per million) relative to the alkylaromatic hydrocarbons; since above this level, water is believed to affect the hydrothermal stability of the molecular-sieve catalyst. At least about 75 mass ppm of water must be supplied to have a significant effect on the process, and the most effective range of trace quantities is from about 100 to 500 mass ppm relative to the alkyaromatic hydrocarbons. The water may be injected into the alkylaromatic feedstock or into the combined reactants to the reaction zone. Alternatively, the water may be supplied as steam in the hydrogen-containing stream.

As will be apparent to the skilled artisan, other compounds besides water itself may be injected where such compounds would effectively form water when provided to the reaction zone while not intending to limit the invention, example water, source compounds which form water in the reaction include but are not limited to alcohols, ethers, esters, etc. A preferred water source compound is methanol.

The water source is continuously provided at the typical operating conditions in the reaction zone. Alternatively, the water source is provided intermittently. The water source can be stopped or provided in various amounts depending on the performance required from the catalyst system in the reaction zone. One measure of catalyst performance is weighted average bed temperature (WABT). When the catalyst is operated to achieve a constant conversion of ethylbenzene, a resulting gradual deactivation requires compensatory WABT adjustment. When WABT becomes too high it can begin to become a limiting control variable based on equipment constraints such as heater duty. Therefore intermittent water injection in the range provided herein above can allow for an extra WABT operating margin to improve the operating cycle of a temperature constrained reactor. Depending on the nature of the feed mixture and the catalyst type and condition, the amount and effectiveness of the trace water will vary. Water already present in the feed as received from the feed source will also periodically require some adjustment to the amount of additional trace water supplied to the reaction zone.

The particular product recovery scheme employed is not deemed to be critical to the instant invention. Any recovery scheme known in the art may be used. Typically, the reactor effluent will be condensed with the hydrogen and light hydrocarbon components removed therefrom by flash separation. The condensed liquid product is then subjected to a fractionation procedure to further purify the desired liquid product Valuable high-purity benzene can be recovered from the light liquid product. In some instances it may be desirable to recover certain product species, such as orthoxylene, by more rigorous fractionation. In most instances a liquid $C_8$ aromatics product is processed to selectively recover the para-xylene isomer. Recovery of para-xylene can be performed by crystallization methods or most preferably by selective adsorption using crystalline aluminosilicates. The raffinate remaining after recovery of the desired xylene isomers may be returned to the isomerization reactor section.

As noted herein above, the present invention is drawn to a process for use in isomerization of $C_8$ aromatics using a non-zeolitic molecular-sieve or zeolitic aluminosilicate catalyst. A component of the catalyst of the present invention therefore is at least one non-zeolitic molecular sieve, usually denoted as "NZMS" and defined in the instant invention to include molecular sieves containing framework tetrahedral units ($TO_2$) of aluminum ($AlO_2$) and phosphorus ($PO_2$) in the form of aluminophosphates as disclosed in U.S. Pat. No. 4,310,440. "NZMS" also includes molecular sieves containing at least one additional element (EL) as a framework tetrahedral unit ($ELO_2$). NZMS includes the "SAPO" molecular sieves of U.S. Pat. No. 4,440,871, "ELAPSO" molecular sieves as disclosed in U.S. Pat. No. 4,793,984 and "MeAPO", "FAPO", "TAPO" and "MAPO" molecular sieves, as hereinafter described. Crystalline metal aluminophosphates (MeAPOs where "Me" is at least one of Mg, Mn, Co and Zn) are disclosed in U.S Pat. No. 4,567,029, crystalline ferroaluminophosphates (FAPOs) are disclosed in U.S. Pat. No. 4,554,143, titanium aluminophosphates (TAPOs) are disclosed in U.S. Pat. No. 4,500,651, MAPO metal aluminophosphates wherein M is As, Be, B, Cr, Ga, Ge, Li or V are disclosed in U.S. Pat. No. 4,686,093, and binary metal aluminophosphates are described in Canadian Patent 1,241,943. ELAPSO molecular sieves also are disclosed in patents drawn to species thereof, including but not limited to GaAPSO as disclosed in U.S. Pat. No. 4,735,806, BeAPSO as disclosed in U.S. Pat. No. 4,737,353, CrAPSO as disclosed in U.S. Pat. No. 4,738,837, CoAPSO as disclosed in U.S. Pat. No. 4,744,970, MgAPSO as disclosed in U.S. Pat. No. 4,758,419 and MnAPSO as disclosed in U.S. Pat. No. 4,793,833. All the aforementioned patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, MeAPO-11 and ELAPSO-31. The preferred elliptical-pore crystalline non-zeolitic molecular sieves are one or more of the AEL framework types, especially SAPO-11, or one or more of the ATO framework types, especially MAPSO-31, according to the "Atlas of Zeolite Structure Types" (Butterworth-Heineman, Boston, Mass., $3^{rd}$ ed. 1992).

In the following discussion on preferred NZMSs, the mole fractions of the NZMSs are defined as compositional values which are plotted in phase diagrams in each of the identified patents or published applications.

The silicoaluminophosphate molecular sieve SAPO-11 described in U.S. Pat. No. 4,440,871, having respective maximum and minimum crystallographic free diameters of 6.3 and 3.9 Å and resulting maximum/minimum ratio of 1.6+, is especially preferred. The silicoaluminophosphate molecular sieves are disclosed as microporous crystalline silicoalumino-phosphates, having a three-dimensional microporous framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from 0.02 to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and represent the following values for "x", "y" and "z":

| Point | Mole Fraction | | |
|---|---|---|---|
| | x | y | z |
| A | 0.01 | 0.47 | 0.52 |
| B | 0.94 | 0.01 | 0.05 |

-continued

| | Mole Fraction | | |
|---|---|---|---|
| Point | x | y | z |
| C | 0.98 | 0.01 | 0.01 |
| D | 0.39 | 0.60 | 0.01 |
| E | 0.01 | 0.60 | 0.39 |

The silicoaluminophosphates of U.S. Pat. No. 4,440,871 are generally referred to therein as "SAPO" as a class, or as "SAPO-n" wherein "n" is an integer denoting a particular SAPO such as SAPO-11, SAPO-31, SAPO-40 and SAPO-41.

A preferred SAPO-11 for use in the present invention is condensed-silica SAPO-11 denoted as SM-3 and prepared in accordance with the teaching of U.S. Pat. No. 5,158,665 (Miller) which is incorporated by reference. SM-3 comprises a $P_2O_5$-to-alumina mole ratio at the surface of the silicoaluminophosphate of about 0.80 or less, preferably from about 0.80 to about 0.55; a $P_2O_5$-to-alumina mole ratio in the bulk of the SAPO of 0.96 or greater, preferably from about 0.96 to 1; and a silica-to-alumina mole ratio at the surface which is greater than in the bulk of the SAPO. Preferably the SM-3 has a composition in terms of mole ratios of oxides on an anhydrous basis of:

$$mR:Al_2O_3:nP_2O_5:qSiO_2$$

wherein "R" represents at least one organic templating agent present in the intracrystalline pore system, "m" represents the moles of "R" present and has a value such that there are from 0.02 to 2 moles of "R" per mole of alumina, n has a value of from 0.96 to 1.1 and preferably 0.96 to 1, and q has a value of from 0.1 to 4 and preferably 0.1 to 1. U.S. Pat. No. 4,943,424 (Miller) is also incorporated herein by reference for its teachings with respect to preparation and properties of the preferred SM-3.

The alternative preferred crystalline non-zeolitic molecular sieves are one or more of the ATO framework types according to the "Atlas of Zeolite Structure Types". The MgAPSO-31 molecular sieve of U.S. Pat. No. 4,758,419, having a crystallographic free diameter of 5.4 Å, is especially preferred. MgAPSO sieves have a framework structure of $MgO_2^{-2}$, $AlO_2^-$, $PO_2^+$, and $SiO_2$ tetrahedral units having an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value of zero to about 0.3; and "w", "x", "y" and "z" represent the mole fractions of elemental magnesium, aluminum, phosphorus and silicon, respectively, present as tetrahedral oxides. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

The MgAPSO-31 molecular sieve preferably has a framework magnesium content of from about 0.003 to 0.035 mole fraction, consistent with the teachings of U.S. Pat. No. 5,240,891 which is incorporated herein by reference thereto.

As noted previously, the present invention is drawn to a process for use in isomerization of C8 aromatics, comprising a non zeolitic molecular sieve or zeolitic aluminosilicate catalyst. Having described the preferred NZMS catalyst embodiment above, the description of the alternate pentasil zeolitic aluminosilicate catalyst embodiment follows below. A component of this catalyst of the present invention preferably comprises at least one pentasil zeolitic aluminosilicate medium-pore molecular sieve. The term "medium-pore" refers to the pore size as determined by standard gravimetric adsorption techniques in the art of the referenced crystalline molecular sieve between what is recognized in the art as "large pore" and "small pore," see Flanigen et al, in a paper entitled, Aluminophosphate Molecular Sieves and the Periodic Table", published in the "New Developments in Zeolite Science and Technology" Proceedings of the 7th International Zeolite Conference, edited by Y. Murakami, A. Iijima and J. W. Ward, pages 103–112 (1986). Intermediate-pore crystalline molecular sieves have pore sizes between 0.4 nm and 0.8 nm, especially about 0.6 nm. For the purposes of this invention, crystalline molecular sieves having pores between about 5 and 6.5 Å are defined as "medium-pore" molecular sieves.

The term "pentasil" of the preferred pentasil zeolite component is used to describe a class of shape-selective zeolites. This class of zeolites is well known to the art and is typically characterized by a silica/alumina mole ratio of at least about 12. Descriptions of the pentasils may be found in U.S. Pat. Nos. 4,159,282; 4,163,018; and 4,278,565, all of which are incorporated herein by reference. Of the pentasil zeolites, the preferred ones are MFI, MEL, MTW, MTT and FER (IUPAC Commission on Zeolite Nomenclature), with MFI-type zeolites, often identified as ZSM-5, being particularly-preferred. It is a preferred embodiment of the present invention that the pentasil be in the hydrogen form. Conversion of an alkali metal form pentasil to the hydrogen form may be performed by treatment with an aqueous solution of a mineral acid. Alternatively, hydrogen ions can be incorporated into the pentasil by ion exchange with ammonium hydroxide followed by calcination.

It is also within the scope of the present invention that the particular pentasil selected may be a gallosilicate. Gallosilicates have essentially the same structure as the preferred zeolites described hereinabove, except that all or part of the aluminum atoms in the aluminosilicate crystal framework are replaced by gallium atoms. This substitution of the aluminum by gallium is usually performed prior to or during synthesis of the zeolite. The gallium content for this particular type of pentasil, expressed as mole ratios of $SiO_2$ to $Ga_2O_3$, ranges from 20:1 to 400:1 or more. The gallium-substituted pentasil zeolite may be prepared by crystallization from a reaction mixture comprising a silica source, a source of $Ga_2O_3$, a source of $Al_2O_3$ if desired, and optionally an organic-template compound.

The non-zeolitic molecular sieve and the zeolitic aluminosilicate each preferably are composited with a binder for convenient formation of catalyst particles. The proportion of NZMS in the first catalyst is about 5 to 90 mass-%, preferably about 10 to 80 mass-%, the remainder other than metal and other components discussed herein being the binder component. The relative proportion of zeolite in the second catalyst may range from about 5 to about 99 mass-%, with about 10 to about 90 mass-% being preferred.

It is within the scope of the invention that a catalytic composition can combine one or more NZMSs with each other or with crystalline zeolitic aluminosilicates. Catalysts containing the more non-zeolitic molecular sieves and zeolitic aluminosilicates may be contained in separate reactors, arranged sequentially in the same reactor, mixed physically, or composited on the same particle.

Considering next the binder utilized in the present invention, the binder should be a porous, adsorptive, high-surface area support having a surface area of about 25 to about 500 $m^2/g$. It is intended to include but not be limited to within the scope of the present invention binder materials which have traditionally been utilized in dual-functional hydrocarbon conversion catalysts such as: (1) silica or silica gel, silicon carbide, clays and silicates including those synthetically prepared and naturally occurring, which may or may not be acid treated, for example, attapulgus clay, diatomaceous earth, fuller's earth, kaolin, kieselguhr, etc.; (2) ceramics, porcelain, bauxite; (3) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, zirconia-alumina, etc.; and (4) combinations of one or more materials from one or more of these groups. The preferred binders for use in the present invention are refractory inorganic oxides, with best results obtained with a binder comprising alumina. Suitable aluminas are the crystalline aluminas known as the gamma-, eta-, and theta-aluminas, with gamma-alumina as the preferred form. In addition, in some embodiments, the alumina binder may contain minor proportions of other well known refractory inorganic oxides such as silica, zirconia, magnesia, etc.; good results may be obtained with a binder containing from about 90 to 99 mass-% alumina and from about 1 to 10 mass-% zirconia. A preferred binder or matrix component is a phosphorus-containing alumina component. The phosphorus may be incorporated in any acceptable manner known in the art. One method of preparing such alumina phosphate is described in U.S. Pat. No. 4,629,717, which is incorporated by reference The preferred alumina binder is uniform in composition and may be prepared in any suitable manner and may be synthetically prepared or naturally occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina binder may be prepared by adding a suitable alkaline reagent, such as ammonium hydroxide to a salt of aluminum such as aluminum chloride, aluminum nitrate, etc., in an amount to form an aluminum hydroxide gel which, upon drying and calcining, is converted to alumina.

An alternative preferred binder is a form of amorphous silica. The preferred amorphous silica is a synthetic, white, amorphous silica (silicon dioxide) powder which is classified as wet-process, hydrated silica. This type of silica is produced by a chemical reaction in a water solution, from which it is precipitated as ultra-fine particles. It is preferred that the BET surface area of the silica is in the range from about 120 to 160 $m^2/g$. The low content of sulfate salts isdesired, preferably less than 0.3 mass-%. It is especially preferred that the amorphous silica binder be nonacidic, e.g., that the pH of a 5% water suspension be neutral or basic (pH about 7 or above).

Using techniques commonly known to those skilled in the art, the catalyst of the present invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing. A preferred shape for the catalyst composite is the extrudate prepared using the well-known extrusion method. Here the molecular sieve is combined with the binder and a suitable peptizing agent and mixed to form a homogeneous dough or thick paste. This material is then extruded through a die pierced with multiple holes and the spaghetti-shaped extrudate is cut off on the opposite side to form short cylinders. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art. The Theological properties of the dough mixture can be varied by the use of "extrusion aids" such as methylcellulose, stearates, small amounts of clay, colloidal silica, etc. After extrusion, the cylinders are dried and calcined as set forth hereinbelow.

An alternative preferred shape of the subject catalyst is a sphere, advantageously manufactured by the well known oil drop method which comprises forming a hydrosol of the desired inorganic oxide binder by any of the techniques taught in the art. For example, alumina hydrosol is preferably prepared by reacting aluminum metal with hydrochloric acid. The molecular sieve is then uniformly dispersed in the hydrosol. This resultant zeolite-containing hydrosol is then commingled with a suitable gelling agent and is dispersed as droplets into an oil bath maintained at elevated temperatures. As discussed later, in one embodiment, the lead component may be added to the mixture prior to forming the droplets and either before, after, or simultaneously with the pentasil. The droplets of the mixture remain in the oil bath until they set and form hydrogel spheres. The spheres are continuously withdrawn from the oil bath and typically subjected to specific aging treatments in oil and an ammoniacal solution to further improve their physical characteristics.

The resulting composites then preferably are washed and dried at a relatively low ternperatu re of about 50–200° C. and subjected to a calcination procedure at a temperature of about 450–700° C. for a period of about 1 to about 20 hours.

The zeolitic aluminosilicate catalyst optimally is subjected to steaming to tailor its acid activity. The steaming may be effected at any stage of the zeolite treatment, but usually is carried out on the composite of zeolite and binder prior to incorporation of the platinum-group metal. Steaming conditions comprise a water concentration of about 5 to 100 volume-%, pressure of from about 100 kPa to 2 MPa, and temperature of between about 600° C. and 1200° C.; the steaming temperature preferably between about 650° C. and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred. Alternatively or in addition to the steaming, the composite may be washed with one or more of a solution of ammonium nitrate, a mineral acid, and/or water. The washing may be effected at any stage of the preparation, and two or more stages of washing may be employed.

Another component of the present invention is one or more of the platinum-group metals, selected from platinum, palladium, rhodium, ruthenium, osmium, and iridium. The preferred platinum-group metal component is platinum, with palladium being the next preferred metal. The platinum-group metal component may exist within the final catalyst composite as a compound such as an oxide, sulfide, halide, oxysulfide, etc., or as an elemental metal or in combination with one or more other ingredients of the catalyst. It is believed that the best results are obtained when substantially all the platinum-group metal component exists in a reduced state. The platinum-group metal component generally comprises from about 0.01 to about 2 mass % of the final catalytic composite, calculated on an elemental basis. Most preferably, the catalyst contains from about 0.05 to 1 mass % platinum.

The platinum-group-metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the sieve component and binder. Complexes of platinum-group metals which may be employed in impregnating solutions, co-extruded with the sieve and binder, or added by other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diaminepalladium (II) hydroxide, tetramminepalladium (II) chloride, and the like. Preferably the platinum-group metal component is concentrated on the binder component of the catalyst by any method known in the art. One method of effecting this preferred metal distribution is by compositing the metal component with the binder prior to co-extruding the sieve and binder It is within the scope of the present invention that the present catalyst composites may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution. The optional metal modifier group component generally comprises from about 0.01 to about 5.0 mass % of the final catalytic composite.

The catalyst of the present invention may contain a halogen component, comprising either fluorine, chlorine, bromine or iodine or mixtures thereof, with chlorine being preferred. Preferably, however, the catalyst contains no added halogen other than that associated with other catalyst components.

The catalyst composite is dried at a temperature of from about 100° to about 320° C. for a period of from about 2 to about 24 or more hours and, usually, calcined at a temperature of from 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere to result in a final composite that contains from about 0.1 to about 2.0 mass % halogen, calculated on an elemental basis.

The resultant calcined composites optimally are subjected to a substantially water-free reduction step to insure a uniform and finely divided dispersion of the optional metallic components. The reduction optionally may be effected in the process equipment of the present invention. Substantially pure and dry hydrogen (i.e., less than 20 vol. ppm H2O) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

EXAMPLES

The following examples will serve to illustrate certain specific embodiments of the present invention. These examples should not, however, be construed as limiting the scope of the invention as set forth in the claims. There are many possible other variations, as those of ordinary skill in the art will recognize, which are within the spirit of the invention.

Example 1

A catalyst (X) was prepared in accordance with the procedures described hereinabove in order to illustrate the advantages of the present invention. MFI zeolite was added to an alumina sol solution, prepared by digesting metallic aluminum in hydrochloric acid, in an amount sufficient to yield a zeolite content in the finished catalyst of about 11 mass %. A second solution of hexamethylenetetramine (HMT) was prepared and added to the zeolite/alumina sol mixture to give a homogeneous admixture. This admixture was then dispersed as droplets into an oil bath maintained at about 93° C. The droplets remained in the oil bath at 150° C. until they set and formed hydrogel spheres. These spheres were removed from the oil bath, water washed with a 0.5% ammonia/water solution, air dried, and calcined at a temperature of about 650° C. These calcined spheres were then co-impregnated with platinum and lead, using a solution of chloroplatinic acid, lead nitrate, and 2 mass % hydrochloric acid. The impregnated spheres were oxidized and chloride adjusted at 525° C., subjected to a reducing environment of H2 at 565° C., and sulfided with $H_2S$ to yield 0.07 mass % sulfur on the catalyst. The final catalyst consisted essentially of about 11 mass % MFI zeolite, 0.21 mass % platinum, 0.67 mass % lead, and 0.78 mass % chloride with the remainder being alumina binder.

Example 2

The catalyst X of Example 1 was evaluated for upgrading of $C_8$ aromatics in a pilot plant. The feedstock composition was approximately as follows in mass %:

benzene 0.1
toluene 0.6
para-xylene 3.6
metaxylene 68.1
orthoxylene 16.9
ethylbenzene 10.3
$C_9$ hydrocarbons 0.4

Feedstock was prepared by stripping in a fractionator and storing under a dry (<1 ppm H2O) nitrogen blanket. Pilot-plant operating conditions comprised a temperature range of about 390°–450° C., a liquid hourly space velocity of about 4 $hr^{-1}$, and a molar ratio of hydrogen gas to hydrocarbon feedstock of about 3 to 5. Pressure was varied from about 4 to 11 atmospheres (gauge) to limit formation of $C_8$ naphthenes as temperature was varied.

The feedstock was processed in the pilot plant over a range of temperatures, varying pressure as described. The temperature survey on fresh catalyst was performed on a dry feedstock without water addition at a gas-to-hydrocarbon ratio of about 3. A subsequent test at low temperature showed severe deactivation, and the testing at dry conditions was discontinued. Trace quantities of water were added to the reactor feed to determine effect on catalyst performance. The initial test and temperature survey showed improved results over even the fresh catalyst, and a one-week stability test at about 435° C. confirmed catalyst stability with trace water addition.

Example 3

The results of the temperature surveys and individual data points are plotted as FIGS. I and II. FIG. I is a plot of the product ratio of para-xylene in total xylenes against reactor temperature. FIG. II shows ethylbenzene conversion as a function of reactor temperature.

Performance of the deactivated catalyst with trace water addition shows a significant benefit over the dry operation, and even over fresh catalyst at higher temperatures. Comparing the dry test (broken line between high temperature on fresh catalyst and return to low temperature) with the test based on water addition, the provision of trace quantities of water on average lowered the temperature required to achieve a given para-xylene yield by about 15–20° C., or alternatively improved the para-xylene content of the xylenes by nearly 3%. Ethylbenzene conversion was increased by 8–20% at the same temperature.

Example 4

A second catalyst (Y) was prepared in accordance with the procedures described hereinabove in order to illustrate the advantages of the present invention where water injection is provided intermittently. SM-3 silicoaluminophosphate was prepared in accordance with the teachings of U.S. Pat. No. 4,943,424 (Miller). The SM-3 was composited with alumina and tetramine platinic chloride. The composite comprised about 60 mass-% SM-3 and 40 mass-% alumina. Tetramine platinic chloride was incorporated into the composition to effect a platinum level of 0.28 mass-% on an elemental basis, and the catalyst was calcined and reduced.

This catalyst was tested in a pilot plant flow reactor processing a non-equilibrium $C_8$-aromatic feed mixture having the following approximate composition in mass-%:

| | |
|---|---|
| $C_6$ hydrocarbons | 0.4 |
| toluene | 0.8 |
| $C_7$ non-aromatic hydrocarbons | 0.4 |
| ethylbenzene | 16.3 |
| para-xylene | 0.2 |
| metaxylene | 48.8 |
| orthoxylene | 23.1 |
| $C_8$ non-aromatic hydrocarbons | 9.7 |
| $C_9$ hydrocarbons | 0.3 |

This feed was contacted with 100 cc of catalyst at a liquid hourly space velocity of 3.0 and a hydrogen/hydrocarbon mole ratio of 4. Reactor temperature was adjusted to maintain a favorable conversion level. Conversion is expressed as the disappearance per pasof ethylbenzene. $C_8$ aromatic loss is primarily to obenzer and tolueqne, with smaller amounts to light gases being produced. The feed containing initial low water at 25 mass-ppm up for the initial part of the experiment. Points 1a and 1b indicate the gradual decline in catalyst performance. The water was then increased to 300 mass-ppm for the middle part. Point 2 indicates the effect of water addition on improving catalyst performance. The final part of the experiment decreased water back to the initial level. Point 3 indicates the rejuvenation of the catalyst and its approach back to initial fresh performance. The above results may be summarized as follows:

| Phase | 1a | 1b | 2 | 3 |
|---|---|---|---|---|
| Temperature, ° C. | 382 | 385 | 386 | 383 |
| Ethylbenzene Conversion | 24 | 21 | 27 | 24 |
| C8-aromatics losses | 2.0 | 2.4 | 1.1 | 1.4 |

We claim as our invention:

1. A process for the isomerization of a non-equilibrium alkylaromatic feed of xylenes and ethylbenzene which consists essentially of contacting the feed with a catalyst comprising from about 0.1 to about 2 mass-% of at least one platinum-group component, an inorganic-oxide binder, and a third component of about 5 to about 90 mass-% selected from the group consisting of at least one non-zeolitic molecular sieve, at least one pentasil zeolitic aluminosilicate selected from the group consisting of MFI, MEL, MMW, MTT and FER, and mixtures thereof, with the addition of a trace water source selected from the group consisting of water, a water forming precursor, and mixtures thereof, in an amount corresponding to about 75 to about 750 mass ppm of equivalent water calculated on the alkylaromatic feed basis, in a reaction zone operated at isomerization conditions in order to produce a near-equilibrium product of xylenes.

2. The process of claim 1 wherein the water source is added continuously.

3. The process of claim 1 wherein the water source is added intermittently.

4. The process of claim 1 wherein the feed is substantially sulfur-free.

5. The process of claim 1 wherein the water source provides from about 100 to about 500 mass ppm of equivalent water calculated on the alkylarmmatic feed-basis.

6. The process of claim 1 wherein the zeolitic aluminosilicate is MFI.

7. The process of claim 1 wherein the non-zeolitic molecular sieve is a crystalline SAPO-11 molecular sieve.

8. The process of claim 7 wherein the crystalline SAPO-11 is an SM-3 molecular sieve.

9. The process of claim 1 wherein the non-zeolitic molecular sieve is a MgAPSO-31 molecular sieve.

10. The process of claim 1 wherein the non-zeolitic molecular sieve is aluminophosphate molecular sieve.

11. The process of claim 1 wherein the isomerization conditions comprise a temperature from about 300° C. to about 600° C., a pressure from about 100 kPa to about 5 Mpa and a liquid hourly space velocity from about 0.5 to about 50 hr$^{-1}$.

12. The process of claim 11 further comprising adding hydrogen in the amount of about 0.5 to about 10 moles per mole of feed.

13. A process for the isomerization of a non-equilibrium alkylaromatic feed of xylenes and ethylbenzene which consists essentially of contacting the feed with a catalyst comprising from about 0.1 to about 2 mas-% of at least one platinum-group component, at least one non-zeohitic molecular sieve, and an Inorganic-oxide binder, with the addition of a trace water source selected from the group consisting of water, a water forming precursor, and mixtures thereof, in an amount corresponding to about 75 to about 750 mass ppm of equivalent water calculated on the alkylaromatic feed basis, in a reaction zone employing isomerization conditions comprising a temperature from about 300° C. to about 600° C., a pressure from about 100 kPa to about 5 Mpa and a liquid hourly space velocity from about 0.5 to about 50 hr$^{-1}$ in order to produce a near equilibrium product of xylenes.

14. The process of claim 13 wherein the water source is added intermittently.

15. The process of claim 13 wherein the water source is added continuously.

16. The process of claim 13 wherein the non-zeolitic molecular sieve is a crystalline SAPO-11 molecular sieve.

17. A process for the isomerization of a non-equilibrium alkylaromatic feed of xylenes and ethylbenzene which consists essentially of contacting the feed with a catalyst comprising from about 0.1 to about 2 mass-% of at least one platinum-group component, from about 5 to about 90 mass % of at least one zeolitic aluminosilicate selected from the group consisting of MFI, MEL, MTW, MTT and FER, and an inorganic-oxide binder, with the addition of a trace water source selected from the group consisting of water, a water forming precursor, and mixtures thereof, in an amount corresponding to about 75 to about 750 mass ppm of equivalent water calculated on the alkylaromatlo feed basis, in a reaction zone employing isomerization conditions comprising a temperature from about 300° C. to about 600° C., a pressure from about 100 kPa to about 5 Mpa and a liquid hourly space velocity from about 0.5 to about 50 hr$^{-1}$ in order to produce a near-equilibrium product of xylenes.

18. The process of claim 17 wherein the water source is added intermittently.

19. The process of claim 17 wherein the water source is added continuously.

20. The process of claim 17 wherein the zeolitic aluminosilicate is MFI.

* * * * *

UNITED STATES PATENT AND TRADEMARK OFFICE
CERTIFICATE OF CORRECTION

PATENT NO.    : 6,512,155 B1                                                         Page 1 of 1
DATED         : January 28, 2003
INVENTOR(S)   : James A. Johnson et al.

It is certified that error appears in the above-identified patent and that said Letters Patent is hereby corrected as shown below:

Column 14,
Line 45, replace "MMW" with -- MTW--.
Line 61, replace "alkylarmmatic" with -- alkylaromatic --.

Column 15,
Line 16, replace "mas-%" with -- mass-% --.
Line 17, replace "non-zeohitic" with -- non-zeolitic --.
Line 18, replace "an Inorganic" with -- an inorganic --.
Line 27, replace "near equilibrium" with -- near-equilibrium --.

Column 16,
Line 16, replace "alkylaromatio" with -- alkylaromatic --.

Signed and Sealed this

Third Day of June, 2003

JAMES E. ROGAN
*Director of the United States Patent and Trademark Office*